United States Patent [19]

Chaumette et al.

[11] Patent Number: 5,302,622

[45] Date of Patent: Apr. 12, 1994

[54] COBALT-BASED CATALYST AND PROCESS FOR CONVERTING SYNTHESIS GAS INTO HYDROCARBONS

[75] Inventors: Patrick Chaumette, Bougival; Catherine Verdon, Rueil Malmaison; Daniel Cruypelinck, Nanteuil Le Haudoin, all of France

[73] Assignee: Institut Francais Du Petrole, Rueil-Malmaison, France

[21] Appl. No.: 57,604

[22] Filed: May 5, 1993

[30] Foreign Application Priority Data

Jul. 27, 1992 [FR] France .............................. 92 09338

[51] Int. Cl.$^5$ .......................... C07C 27/00; C07C 1/00
[52] U.S. Cl. .................... 518/713; 518/715; 518/717; 585/700; 585/733
[58] Field of Search ............... 585/700, 733; 518/713, 518/715, 717

[56] References Cited

FOREIGN PATENT DOCUMENTS

| | | |
|---|---|---|
| 46119 | 8/1985 | Australia . |
| 1177854 | 11/1984 | Canada . |
| 0142887 | 5/1985 | European Pat. Off. . |
| 2388781 | 11/1978 | France . |
| 855317 | 7/1985 | South Africa . |
| 1548468 | 11/1977 | United Kingdom . |
| 2103649 | 2/1983 | United Kingdom . |
| 2149812 | 6/1985 | United Kingdom . |
| 85/04598 | 4/1985 | World Int. Prop. O. . |

*Primary Examiner*—Patrick P. Garvin
*Assistant Examiner*—E. D. Irzinski
*Attorney, Agent, or Firm*—Millen, White, Zelano, & Branigan

[57] ABSTRACT

The invention relates to a process for the conversion of synthesis gases into a mixture of essentially linear and saturated hydrocarbons, characterized by the use of a catalyst prepared by a gelling procedure, incorporating cobalt, copper and ruthenium, the cobalt, copper and ruthenium being dispersed on a support having at least one oxide of a metal chosen from within the group formed by silica and alumina, the cobalt content, expressed by cobalt weight based on the catalyst weight, being between 1 and 60% by weight, the ruthenium content, expressed by ruthenium weight based on the cobalt weight, being between 0.1 and 20%, and the copper weight, expressed by copper weight based on the cobalt weight, being between 0.1 and 10%.

15 Claims, No Drawings

COBALT-BASED CATALYST AND PROCESS FOR CONVERTING SYNTHESIS GAS INTO HYDROCARBONS

BACKGROUND OF THE INVENTION

The present invention relates to a process for producing hydrocarbons from CO—($CO_2$)—$H_2$ mixtures, i.e. CO—$H_2$ mixtures optionally incorporating $CO_2$ and referred to as synthesis gases. It more particularly relates to the use of a catalyst making it possible to convert the synthesis gas into a mixture of essentially $C_5+$ hydrocarbons (i.e. having at least 5 carbon atoms per molecule) usable as a fuel or fuel oil.

The expert knows that synthesis gas can be converted into hydrocarbons in the presence of catalysts containing transition metals. This reaction, generally performed at a temperature between 150° and 350° C. and under pressure, is known as the FISHER-TROPSCH synthesis. The catalysts normally used for the transformation of CO—($CO_2$)—$H_2$ mixtures into liquid or gaseous hydrocarbons generally incorporate at least one metal of the VIII group, such as iron, ruthenium, cobalt or nickel.

Products prepared by FISCHER-TROPSCH synthesis in the presence of these metal catalysts have a very broad molecular weight distribution. Thus, only a small proportion of the products obtained falls within the middle distillates range constituted by kerosene and gas oil fractions, the kerosene fraction or fractions being constituted by a mixture of hydrocarbons having boiling points between 140° and 300° C. and the gas oil fraction or fractions being constituted by a mixture of hydrocarbons having boiling points between 180° and 370° during an atmospheric distillation, such as is performed by the Expert on a petroleum crude.

Considerable efforts have been made since 1973 to improve the middle distillates efficiency of processes based on the conversion of synthesis gases. In particular cobalt, which has been known as a constituent of Fischer-Tropsch catalysts since the early works of SABATIER and SENDERENS (J. Soc. Chem. Ind., 21, 504, 1902) and German patents 29, 787 (1913) and 295,202 (1914) has again been used recently as a main constituent of improved catalytic formulations.

These formulations permit the synthesis of essentially paraffinic and linear hydrocarbons. However, a considerable proportion of these hydrocarbons constitutes paraffins having high boiling points, i.e. beyond the range of middle distillates. It is then advantageous to treat these high boiling point hydrocarbons in a hydrocracking process conveniently used in connection with the treatment of heavy fractions obtained from a petroleum crude, in order to improve the overall middle distillate efficiency.

Among the improved formulations referred to hereinbefore, French patent 2,388,781 claims a process for the preparation of hydrocarbons using a catalyst containing 5 to 50% by weight of one or more metals from the iron group, including cobalt and/or 0.1 to 5% by weight ruthenium and 5 to 50% by weight copper and/or zinc, said catalysts being prepared by impregnation. This process makes it possible to prepare hydrocarbons by the catalytic reaction of carbon monoxide with hydrogen, the $H_2$/CO molar ratio being below 1.

French patent 2,370,712 describes the use in a hydrocarbon synthesis process of a catalyst having 10 to 75% by weight of one or more metals from the iron group, as well as 1 to 50% by weight of one or more promoters, including alkaline earth or alkali metals, Ti, Zr, Al, Si, Cu, Ag, Ce, etc. This catalyst is prepared by impregnating a porous support with one or more aqueous solutions of salts of the metals of the iron group and promoters.

Austrian patent 46119/85 describes a catalyst active in Fischer-Tropsch synthesis containing (a) cobalt or a cobalt-based material, (b) silica or a silica precursor and (c) a base or an alkaline material, in which the ratio a:b:c is in the range 1:0.1-100:0.1-100. Said catalyst is prepared by hydrothermal synthesis under pressure and at a temperature between 50° and 500° C.

The conversion of synthesis gas into diesel fuels is also described South African patent 855,317. The latter describes catalyst essentially containing cobalt and ruthenium dispersed on a random support to which has optionally been added a promoter chosen from within groups IIIB or IVB, oxides of actinides or lanthanides, $ZrO_2$ and $TiO_2$ being preferred, as well as catalysts essentially containing cobalt and a promoter chosen from within the group constituted by Rh, Pt, Pd, Ir, Os, Ag and Au.

These catalytic formulations are prepared by impregnating the support with an organic solution containing soluble salts of the different elements entering into the composition of these catalysts.

French patent application 91/07,634 describes catalysts containing cobalt, at least one additional element M chosen from within the group constituted by molybdenum and tungsten and at least one element N chosen from among various elements, including ruthenium and copper, the elements being dispersed on a support. Their formulation differs rom that of the catalysts according to the invention described hereinafter by the obligatory presence of molybdenum and/or tungsten, which leads to the formation of a larger proportion of olefins and/or to slightly lower activities.

Patent WO 85/04598 describes a synthesis gas conversion catalyst and the process for preparing said catalyst comprising a hydrolysis stage, e.g. of a compound of silicon or aluminum. This catalyst contains at least one metal chosen from within the groups VIa and VIII of the periodic classification of elements. It does not contain a group Ib element. Moreover, the preferred formulations described in this patent are essentially iron-based. The hydrolysis of the compounds must be carried out for a sufficiently long time (1 to 12 hours) to be essentially total, rapid gelling leading to a catalyst in which the various elements are not homogeneously distributed. The hydrolysis medium and the hydrolyzed species (not containing a silica and/or alumina-based matrix and other elements) are then separated, e.g. by evaporation and then the gel is thermally treated at between 100° and 600° C.

SUMMARY OF THE INVENTION

A catalytic composition has now been found which, after reducing under hydrogen, leads to a higher conversion activity of the synthesis gas i.e. a CO—($CO_2$)—$H_2$ mixture, into a mixture of essentially linear and saturated hydrocarbons containing at least 80% by weight, based on all the hydrocarbons formed, of a fraction incorporating $C_5+$ hydrocarbons, with less than 10% by weight of olefins in said $C_5+$ fraction.

The catalyst according to the invention contains cobalt, copper and ruthenium and optionally at least one additional element P chosen from elements by groups Ia and IIa of the periodic classification of elements, such as Li, Na, K, Rb, Cs, Be, Mg, Ca, Sr and Ba. Preferably, element P is chosen from among Na, K, Rb, Mg, Ca and Sr, all of these elements being dispersed on a support. The catalyst is at least partly prepared by an impregnation procedure or by a gelling procedure, preferably being completely prepared b a gelling procedure. The support used comprises silica and/or alumina and optionally at least one compound of at least one element Q chosen from Si, Ti, Zr, Sn or Zn.

The cobalt content of the catalyst after calcination (heat treatment at between 100° and 600° C.), expressed as weight of the element based on the weight of the catalyst, is normally between 1 and 60 and preferably between 15 and 40% by weight.

The copper, ruthenium and additional elements or elements P are incorporated in proportions such that: the ruthenium content, expressed as ruthenium weight present in the catalyst based on the cobalt weight present in the catalyst, is between 0.1 and 20 and preferably between 1 and 5%; the copper content, expressed as copper weight present in the catalyst based on the cobalt weight present in the catalyst, is between 0.1 and 10%, preferably between 0.5 and 8% and in even more preferred manner between 1 and 8%; the content of element or elements P, expressed as weight of element or elements P present in the catalyst based on the cobalt weight present in the catalyst is between 0 and 9% and preferably between 0 and 7%.

Thus, as a function of the optional presence of respectively one or more additional element or elements P, said content is respectively the content of the element P or the sum of the contents of the elements P.

The catalyst according to the invention is preferably prepared by a gelling procedure making it possible to incorporate the cobalt, the ruthenium, the copper and optionally at least one compound of element P and optionally at least one compound of element Q in an alcogel formed from a hydrolyzable compound of silicon and/or aluminum and optionally at least one hydrolyzable compound of element Q. This hydrolysis reaction is performed rapidly, the gelling tie being equal to or below 30 min and preferably equal t or below 20 min.

The compounds of cobalt, ruthenium, copper and optionally element or elements P and/or Q which can be used in this preparation procedure are e.g. halides, nitrates, acetates, oxalates, sulphates, complexes formed with oxalic acid and oxylates, complexes formed with citric acid and citrates, complexes formed with tartaric acid and tartrates, complexes formed with acetyl acetonates or any other inorganic or metalorganic derivative containing these elements.

The hydrolyzable compounds of silicon and/or aluminum and optionally silicon, aluminum, titanium, zirconium, tin and zinc usable in this preparation procedure are e.g. alkoxides, carboxylates or any metalorganic complex soluble in an organic solvent and hydrolyzable.

A preferred preparation procedure consists of mixing a solution A containing a hydrolyzable compound of silicon and/or aluminum and optionally at least one hydrolyzable compound of an element Q, preferably one or more alkoxides dissolved in an organic solvent, preferably an alcohol, and an aqueous solution B containing a cobalt compound, a copper compound, a ruthenium compound and optionally a compound of at least one of the elements P and/or Q and optionally containing a mineral acid, which speeds up gelling, such as for example nitric, hydrochloric, sulphuric, phosphoric or boric acid.

The mixing of solutions A and B, accompanied by stirring at a temperature between 20° and 80° C., leads to a mass alcogel formed in less than 30 mn, said alcogel confining virtually the entire original solution and therefore almost all the compounds initially dissolved in solutions A and B. The thus obtained alcogel is then optionally dried at a temperature between 20° and 200° C. and then calcined, e.g. under a flow of air or nitrogen, up to a temperature between 100° and 600° C.

Another method for preparing the catalysts according to the invention consists of preparing a silica and/or alumina hydrogen containing cobalt, copper, ruthenium and optionally at least one element P and/or Q by titrating an aqueous solution of one or more silicon and/or aluminum salts by an appropriate acid or basic solution. Thus, an aqueous acid solution e.g. containing a silicon and/or aluminum compound, e.g. chosen from within the group constituted by silicic acid, aluminum sulphate, aluminum nitrate, aluminum chloride can be titrated by a basic solution e.g. containing sodium hydroxide, ammonium hydroxide, or an alkali metal aluminate and/or silicate (route 1).

It is also possible to titrate a basic solution e.g. containing an alkali metal aluminate and/or silicate by an acid solution e.g. containing hydrochloric or nitric acid (route 2).

Therefore the catalysts according to the invention can be prepared by dissolving compounds of cobalt, copper or ruthenium and optionally elements P and/or Q in one and/or the other of the acid and/or basic solutions and by carrying out one of the titrations described hereinbefore (route 1 or 2) with these acid and basic solutions. This titration is preferably carried out by simultaneously introducing the acid and basic solutions into a reactor in order to perform gelling at a constant pH between 3.5 and 10 and preferably between 5 and 10, the gelling temperature being between 20° and 90° C. and the gelling time below 30 min. An aging is then optionally carried out while allowing the product to evolve at a temperature between 20° and 90° C. in the presence of the gelling solution (mother liquors) or an aqueous solution containing a basic salt, e.g. NaOH or KOH, having a pH between 10 and 12. The hydrogen is then filtered, e.g. washed with water, optionally dried between 20° C. and 200° C. and then calcined, e.g. under an air or nitrogen flow, to a temperature between 100° and 600° C.

Another preferred preparation method consists of dissolving the compounds of cobalt, copper, ruthenium and optionally elements and/or Q in water, then adding, accompanied by stirring, a colloidal silica solution, which is either of a commercial nature or which has been previously prepared according to one of the titration methods described hereinbefore, and an acid solution, e.g. pure or diluted hydrochloric or nitric acid, while maintaining the pH of the mixture at between 0.5 and 4, and preferably between 1 and 3. A complimentary colloidal silica solution fraction is then added in order to progressively increase the pH of the solution to between 3 and 8 pH units, e.g. between 4 and 8 pH units and preferably between 4 and 7 or 5 and 7 pH units. After stirring for less than 30 mm at a temperature between 5° and 90° C., preferably between 20° and 60° C., a silica gel is formed, which contains salts of cobalt copper, ruthenium and optional elements P and/or Q.

This gel is then preferably filtered, washed e.g. with water, optionally dried at between 20° and 200° C. and then calcined, e.g. under an air or nitrogen flow, to a temperature between 100° and 600° C.; It is also possible to prepare an alcogel or a hydrogen containing silicon and/or aluminum and optionally elements P and/or Q and then, before heat treatment, to resuspend said gel in an aqueous or organic solution containing cobalt, copper, ruthenium and optionally elements P and/or Q in excess compared with the quantities desired in the final catalyst. The pH of the solution is optionally adjusted by means of an acid or a base and is preferably between 4 and 8, the temperature being between 25° and 100° C. The gel+solution mixture is stirred for a sufficiently long period, e.g. 30 min to 5 hours, in order to incorporate the desired quantity of cobalt, copper, ruthenium and optionally elements P and/or Q into the gel. The thus obtained gel is optionally washed and then eat treated at between 100° and 600° C.

The catalyst can optionally be shaped by any known process, e.g. by extrusion, drop coagulation drageification, pelletizing or spray drying. Following said shaping phase, the catalyst optionally undergoes a final thermal activation (optional drying and then calcination) under the indicated operating conditions.

The catalyst prepared according to the operating procedures of the invention described hereinbefore is particularly suitable for use in processes for the production, from a synthesis gas, of a mixture of essentially linear and saturated hydrocarbons, containing at least 80% by weight, based on all the hydrocarbons formed, of a fraction incorporating $C_5+$ hydrocarbons and less than 10% by weight of olefins in said $C_5+$ fraction. Therefore the present invention also relates to a process for the synthesis of hydrocarbons from synthesis gas, in the presence of a catalyst prepared according to the invention.

The conditions for using the catalyst S for the production of hydrocarbons will now be described. The catalyst, fed into a reactor, is firstly prereduced by contacting with a mixture of inert gas (e.g. nitrogen) and at least one reducing compound (e.g. carbon monoxide and/or hydrogen), the molar ratio of the reducing compound to the (reducing compound+inert gas) being between 0.001:1 and 1:1.

Prereduction is performed at between 150° and 600° C., preferably between 200° and 500° C., at between 0.1 and 10 MPa and at a space velocity of 100 to 40,000 volumes of mixture per volume of catalyst and per hour. This prereduction is preferably performed in the liquid phase, if subsequently the hydrocarbon synthesis reaction is performed in the liquid phase. The liquid phase of the prereduction can be constituted by at least one hydrocarbon incorporating at least 5 carbon atoms per molecule.

It can also be advantageous to reoxidize the catalyst under a flow of oxygen or air diluted by nitrogen at between 30° and 650° C. and preferably between 50° and 450° C., at a pressure between 0.1 and 1 MPa and a space velocity of 100 to 40,000 volumes of catalyst and per hour, then carry out a further prereduction under the conditions indicated hereinbefore.

The conversion of the synthesis gas into hydrocarbons is then carried out under a total pressure normally between 0.1 and 15 MPa, preferably between 0.5 and 10 MPa, the temperature generally being between 150° and 350° C. and preferably 170° and 300° C.

The space velocity is normally between 10 and 10,000 volumes of synthesis gas per volume of catalyst and per hour and is preferably between 400 and 5,000 volumes of synthesis gas per catalyst volume and per hour, while the $H_2$:CO ratio in the synthesis gas is normally between 1:1 and 3:1, preferably between 1.2:1 and 2.5:1.

The catalyst can be used in calibrated fine powder form (normally 10 to 700 μm) or in the form of particles with an equivalent diameter generally between 2 and 10 mm, in the presence of a gas phase, or a liquid phase (under the operating conditions) and a gas phase. The liquid phase can be one or more hydrocarbons having at least 5 and preferably at least 10 carbon atoms per molecule.

The catalyst according to the invention is particularly active and stable in the reaction of synthesizing hydrocarbons from synthesis gases. It makes it possible to obtain essentially paraffinic hydrocarbons, whose fraction having the highest boiling points can be converted with a high efficiency into middle distillates (gas oil and kerosene fractions) by a hydroconversion process, such as catalytic hydrocracking and/or hydroisomerization.

The following examples illustrate the invention without limiting its scope.

EXAMPLE 1: Catalyst A

A solution 1 containing 135 g of ethyl orthosilicate (T.E.O.S.) dissolved in 50 ml of ethanol and a solution 2 containing 37 g of cobalt nitrate hexahydrate, 0.31 g of ruthenium trichloride hexamine, 2.1 g of copper nitrate trihydrate, 1.2 g of potassium nitrate and 36.2 of concentrated nitric acid dissolved in 80 cm³ of water are mixed under strong stirring and at ambient temperature. Hydrolysis of T.E.O.S. leads, after 15 mn, to the formation of a mass gel containing cobalt, ruthenium, copper and potassium salts.

The gel obtained is separated from the mother liquors, dried in the oven at between 40° and 120° C. and then calcined at 500° in air. 50 g of catalyst A in oxide form and having the composition indicated in table 1 are then obtained.

EXAMPLE 2: Catalyst B

To a solution containing 40 g of cobalt nitrate hexahydrate, 1 g of ruthenium trichloride hexamine and 0.30 g of copper nitrate trihydrate dissolved in 50 ml of water are progressively and simultaneously added 75 g of a colloidal silica solution with 40% by weight $SiO_2$ (LUDOX AS40) and 2 ml of 10% nitric acid so as to maintain the pH of the solution at between 1 and 2. Stirring of the solution is maintained for 10 mn, followed by the addition of 25 g of LUDOX AS40, the pH evolving so as to stabilize at between 5.5 and 6.5 pH units. After 12 mn, a silica gel containing the cobalt, copper and ruthenium salts is formed.

The gel obtained is separated form the mother liquors by filtration, washed with water, dried in the oven at between 40° and 120° C. and then calcined at 500° C. in air. 40 g of catalyst B in oxide form and having the composition indicated in table 1 are then obtained.

EXAMPLE 3: Catalyst C

The preparation of catalyst C differs form that of catalyst A, in that working takes place with 62 g of cobalt nitrate hexahydrate, 0.60 g of ruthenium trichloride dihydrate, 1.2 g of copper nitrate dihydrate and 0.27 g of strontium nitrate, but without adding nitric acid to solution 2 and in that solution 1 only contains 112 g of T.E.O.S. dissolved in 40 ml of ethanol. The catalyst C, in oxide form, obtained in this way has the composition given in table 1.

EXAMPLE 4: Catalyst D

The preparation of catalyst D differs from that of catalyst C in that solution 1 contains 90 g of T.E.O.S. dissolved in 30 ml of ethanol and solution 2 contains 87 g of cobalt nitrate hexahydrate, 1.1 g of ruthenium trichloride hexamine and 0.6 g of copper nitrate trihydrate. Catalyst D, in oxide form, obtained in this way has the composition given in table 1.

EXAMPLE 5: Catalyst E

The preparation of catalyst E differs from that of catalyst C in that solution 1 contains 100 g of T.E.O.S. and solution 2 contains 20 g of aluminum nitrate having 9 water molecules in place of strontium nitrate. The catalyst E, in oxide form, obtained in this way has the composition given in table 1.

EXAMPLE 6: Catalyst F

The preparation of catalyst F differs from that of catalyst C in that solution 1 contains 95 g of T.E.O.S. and solution 2 contains 11.8 g of zirconyl nitrate dihydrate in place of strontium nitrate. Catalyst F, in oxide form obtained in this way, has the composition given in table 1.

EXAMPLE 7: Catalyst G

The preparation of catalyst G differs from that of catalyst B in that the solution contains 49 g of cobalt nitrate hexahydrate, 0.5 g of ruthenium trichloride dihydrate, 0.95 g of copper nitrate dihydrate and 54 g of a 15% by weight aqueous titanium trichloride solution. The colloidal silica solution quantity added is 90 g. Catalyst G, in oxide form obtained in this way, has the composition given in table 1.

EXAMPLE 8 (comparative): Catalyst H

The preparation of catalyst H differs from that of catalyst D in that 87 g of cobalt nitrate hexahydrate and 1.1 g of ruthenium trichoride hexamine are introduced into solution 2. Catalyst H, in oxide form, obtained in this way has the composition given in table 1.

EXAMPLE 9 (comparative): Catalyst I

The preparation of catalyst I differs from that of catalyst D in that introduction takes place into solution 2 of 86.5 g of cobalt nitrate hexahydrate and 0.60 g of copper nitrate dihydrate. Catalyst I, in oxide form obtained in this way, has the composition indicated in table 1.

EXAMPLE 10 (comparative): Catalyst J

The preparation of catalyst J differs from that of catalyst D in that solution 1 contains 85 g of T.E.O.S. and in that 86.5 g of cobalt nitrate hexahydrate, 1.4 g of ammonium heptamolybdate tetrahydrate, 1.1 g of ruthenium trichloride hexamine and 0.6 g of copper nitrate trihydrate are introduced into solution 2. The thus obtained catalyst J, in oxide form, has the composition given in table 1.

EXAMPLE 11 (comparative): Catalyst K

A silica support is impregnated (stage a) by an aqueous cobalt nitrate hexahydrate solution having a volume equal to the porous volume of the support and containing 20% by weight cobalt, based on the silica weight and the solution is slowly evaporated to dryness at 80° C. (stage b). The thus obtained impregnated silica is then dried for 1 hour at 100° C. (stage c) and for 16 hours at 150° C. (stage d), followed by calcination for 3 hours at 500° C. (stage e).

This is followed by the deposition of 40% by weight supplementary cobalt in $2 \times 20\%$ by weight, twice repeating the procedure of stages a) to e). For the second impregnation, the considered porous volume is that of the support impregnated by 20% cobalt. Finally, deposition takes place of 8% by weight cobalt, 2.1% by weight ruthenium in the form of ruthenium trichloride dihydrate and 0.7% by weight in the form of copper nitrate dihydrate in accordance with the procedure of stages a) to e) and considering that the porous volume is that of the support impregnated by 40% by weight cobalt.

Catalyst K, in oxide form, obtained in this way has the composition given in table 1.

EXAMPLE 12 (comparative): Catalyst L

The preparation of catalyst L differs from that of catalyst D in that 5.5 g of dissolved potassium nitrate are also added to solution 2. This gives 3.9% by weight K, based on the total catalyst weight, i.e. a K:Co ratio of 11. The thus obtained catalyst L, in oxide form, has the composition indicated in table 1.

EXAMPLE 13

Catalysts A to L, whose preparations are described in examples 1 t 12, were tested in the gas phase in a slurry-type pilot unit operating continuously and with 100 cm$^3$ of catalyst.

Catalysts A to L are previously reduced in situ to 240° C. by a mixture of hydrogen and nitrogen containing 6% hydrogen in nitrogen and then by pure hydrogen up to 350° C. and at atmospheric pressure.

The test conditions for catalysts A to L are as follows: p1 temperature between 200° and 250° C., pressure 2 MPa,
gaseous hourly space velocity (GHSV) 1000 h$^{-1}$,
H$_2$:CO=2:1,
catalyst suspended in a paraffin solvent (C$_{15}$-C$_{40}$ paraffinic fraction) at a concentration of 10% by weight catalyst, based on the suspension weight.

The temperature of the catalytic suspension is reduced to 170° C. and the hydrogen-nitrogen mixture is substituted by pure nitrogen. The pressure is then raised to 2 MPa in the reactor and the synthesis gas (carbon monoxide-hydrogen mixture with a H$_2$:CO ratio of 2:1) is then progressively introduced in order to obtain the hourly volumetric rate (HVR) of 1000 h$^{-1}$.

The nitrogen flow rate is then progressively eliminated and the temperature adjusted to the desired value (table 2: T=200 to 250° C.) with a temperature rise rate of 6° C./mn. The catalytic performance characteristics obtained after stabilization under the synthesis gas are given in table 2.

Table 2 shows that the catalysts according to the invention make it possible to achieve high monoxide (CO) conversion levels. It also shows that more than 80% by weight of the hydrocarbons formed with the catalysts according to the invention belong to the fraction incorporating hydrocarbons having at least 5 carbon atoms per molecule (C$_5$+ hydrocarbons) and that these catalysts lead to the formation of less than 10% by weight olefins in said C$_5$+ fraction. An important proportion of the hydrocarbons formed is consequently within the middle distillate range (kerosene, gas oil) or of paraffins which are solid at ambient temperature (waxes). The distribution of the hydrocarbons obtained is consequently very suitable for the preparation of middle distillates, the hydrocarbon fraction having the highest boiling points being convertable, with high yield, into middle distillates by a hydroconversion process, such as catalytic hydrocracking and/or hydroisomerization. The comparative examples of table 2 also indicate that catalysts H to K and more particularly catalyst K are less active and that catalysts H, I, J and L lead to the formation of significant olefin quantities in the $C_5+$ fraction. Moreover, catalyst I leads to the formation of an insufficient quantity of $C_5+$ hydrocarbons.

TABLE 1

COMPOSITION OF THE CATALYSTS

| Example | Catalyst | % Co (1) | % Ru (1) | % Cu (1) | P | % P (1) | Support | Q | % Q (2) |
|---|---|---|---|---|---|---|---|---|---|
| 1 | A | 15 | 0.2 | 1.1 | K | 0.9 | SiO$_2$ | — | — |
| 2 | B | 20 | 0.8 | 0.2 | — | — | SiO$_2$ | — | — |
| 3 | C | 25 | 0.5 | 0.6 | Sr | 0.2 | SiO$_2$ | — | — |
| 4 | D | 35 | 0.7 | 0.3 | — | — | SiO$_2$ | — | — |
| 5 | E | 25 | 0.5 | 0.6 | — | — | SiO$_2$ | Al | 5 |
| 6 | F | 25 | 0.5 | 0.6 | — | — | SiO$_2$ | Zr | 15 |
| 7 | G | 25 | 0.5 | 0.6 | — | — | SiO$_2$ | Ti | 7 |
| 8 | H (comp.) | 35 | 0.7 | 0 | — | — | SiO$_2$ | — | — |
| 9 | I (comp.) | 35 | 0 | 0.3 | — | — | SiO$_2$ | — | — |
| 10 | J (comp.) | 35 | 0.7 | 0.3 | Mo | 1.5 | SiO$_2$ | — | — |
| 11 | K (comp.) (imp.) | 35 | 0.7 | 0.3 | — | — | SiO$_2$ | — | — |
| 12 | L (comp.) | 35 | 0.7 | 0.3 | K | 3.9 | SiO$_2$ | — | — |

(1) $\frac{\text{Weight of Co or Ru or Cu or P}}{\text{Total catalyst weight}} \times 100$ (2) $\frac{\text{Q weight}}{\text{SiO}_2 \text{ weight}} \times 100$

TABLE 2

CONVERSION OF SYNTHESIS GAS INTO HYDROCARBONS

| Catalyst | Temperature | CO Conv. (vol. %) | Distribution of hydrocarbons formed (wt. %) | | | |
|---|---|---|---|---|---|---|
| | | | C$_1$ | C$_2$-C$_4$ | C$_5$+ | % olefins in C$_5$+ |
| A | 250° C. | 65 | 12.8 | 5.7 | 81.5 | 8.4 |
| B | 240° C. | 68 | 10.3 | 4.5 | 85.2 | 6.2 |
| C | 240° C. | 75 | 5.7 | 2.5 | 91.8 | 8.9 |
| D | 235° C. | 78 | 7.9 | 3.5 | 88.6 | 4.1 |
| E | 240° C. | 82 | 11.8 | 5.1 | 83.1 | 4.5 |
| F | 235° C. | 68 | 10.8 | 4.7 | 84.5 | 5.2 |
| G | 235° C. | 72 | 9.2 | 4.0 | 86.8 | 6.3 |
| H (comp.) | 235° C. | 52 | 7.3 | 3.2 | 89.5 | 13.5 |
| I (comp.) | 235° C. | 34 | 18.7 | 10.1 | 71.2 | 22.7 |
| J (comp.) | 235° C. | 65 | 7.2 | 3.1 | 89.7 | 27.6 |
| K (comp.) | 235° C. | 17 | 8.5 | 4.2 | 87.3 | 3.5 |
| L (comp.) | 235° C. | 37 | 4.1 | 1.8 | 94.1 | 37.2 |

We claim:

1. A process for the conversion of synthesis gases into a mixture of essentially linear and saturated hydrocarbons, comprising subjecting said gases to conversion conditions in the presence of a catalyst prepared by a gelling procedure and incorporating cobalt, copper and ruthenium, the cobalt, copper and ruthenium being dispersed on a support having at least one oxide of silica or alumina, the cobalt content, expressed as cobalt weight present in the catalyst based on the catalyst weight, being between 1 and 60% by weight, the ruthenium content, expressed as ruthenium weight present in the catalyst based on the cobalt weight present in the catalyst, being between 0.1 and 20%, and the copper content, expressed as copper weight present in the catalyst based on the cobalt weight present in the catalyst, being between 0.1 and 10%.

2. A process according to claim 1, wherein the catalyst further comprises at least one additional element P dispersed on the support, said element P being a group Ia or IIa element, the content of element or elements P, expressed by the weight of the element or elements P present in the catalyst, based on the cobalt weight present in the catalyst, being between 0 and 9%.

3. A porous according to claim 2, wherein the content of the element or elements P is between 0 and 7%.

4. A process according to claim 1, wherein the catalyst support further comprises at least one compound of at least one element Q which is Si, Al, Ti, Zr, Sn or Zn.

5. A process according to claim 1, wherein the ruthenium content is between 1 and 5% and the copper content is between 0.5 and 8%.

6. A process according to claim 1, wherein the duration o the preparation by gelling of the catalyst is equal to or below 30 min.

7. A process according to claim 1 wherein the mixture of essentially linear and saturated hydrocarbons contains at least 80% by weight, based on all the hydrocarbons formed, of a fraction incorporating C$_5$+ hydrocarbons and less than 10% by weight olefins in said C$_5$+ fraction.

8. A process according to claim 1, wherein the catalyst undergoes a prereduction prior to use, said catalyst prereduction being carried out by contacting the catalyst with a mixture of inert gases and at least one reducing compound in a molar ratio of between 0.001:1 and 1:1, said reducing compound being carbon monoxide or hydrogen, prereduction being performed at between 150° and 600° C., at between 0.1 and 10 MPa and a hourly volumetric rate between 100 and 40,000 volumes of mixture per volume of catalyst and per hour.

9. A process according to claim 1, wherein the conversion conditions are a pressure between 0.1 and 15 MPa, a temperature between 150° and 350° C., a space velocity of 100 to 10,000 volumes of synthesis gas per volume of catalyst and per hour and a $H_2$:CO molar ratio between 1:1 and 3:1.

10. A process according to claim 1, wherein the conversion is performed in the presence of a liquid phase incorporating at least one hydrocarbon containing at least 5 carbon atoms per molecule.

11. A process according to claim 2, wherein element P is Na, K, Rb, Mg, Ca or Sr.

12. A process according to claim 1, wherein the ruthenium content is 1-5%.

13. A process according to claim 1, wherein the copper content is 0.5-8%.

14. A process according to claim 1, wherein the copper content is 1-8%.

15. A process according to claim 1, wherein the duration of the preparation by gelling of the catalyst is equal to or below 20 min.

* * * * *